(12) United States Patent
Weber et al.

(10) Patent No.: US 11,589,789 B2
(45) Date of Patent: Feb. 28, 2023

(54) DEVICE FOR MEASUREMENT, DIAGNOSIS AND/OR THERAPY OF THE STRENGTH OF THE HUMAN FINGER, HAND, ARM AND/OR SHOULDER

(71) Applicants: Constanze Anna Maria Weber, Dresden (DE); Cornelius Adrian Maria Weber, Meissen (DE)

(72) Inventors: Hansjoerg Weber, Meissen (DE); Cornelius Weber, Meissen (DE)

(73) Assignees: Constanza Anna Maria Weber, Dresden (DE); Cornelius Adrian Maria Weber, Meissen (DE)

( * ) Notice: Subject to any disclaimer, the term of this patent is extended or adjusted under 35 U.S.C. 154(b) by 449 days.

(21) Appl. No.: 16/302,431

(22) PCT Filed: May 11, 2017

(86) PCT No.: PCT/EP2017/061344
§ 371 (c)(1),
(2) Date: Nov. 16, 2018

(87) PCT Pub. No.: WO2017/198543
PCT Pub. Date: Nov. 23, 2017

(65) Prior Publication Data
US 2019/0209068 A1     Jul. 11, 2019

(30) Foreign Application Priority Data
May 17, 2016   (DE) ..................... 10 2016 208 443.7

(51) Int. Cl.
*A61B 5/22*     (2006.01)
*A61B 5/00*     (2006.01)
(Continued)

(52) U.S. Cl.
CPC .............. *A61B 5/225* (2013.01); *A61B 5/224* (2013.01); *A61B 5/6824* (2013.01);
(Continued)

(58) Field of Classification Search
CPC ....... A61B 5/224; A61B 5/225; A61B 5/6824; A61B 5/6825; A61B 5/6826;
(Continued)

(56) References Cited

U.S. PATENT DOCUMENTS 3,680,386 A        8/1972  Cannon
5,471,996 A  *  12/1995  Boatright ............... A61B 5/225
                                                                    33/511
(Continued)

FOREIGN PATENT DOCUMENTS

DE          204 206       11/1983
DE         36 34 940      10/1986
(Continued)

OTHER PUBLICATIONS

Liu Pu et al., "EMG-force estimation for multiple finders", 2013 IEEE Signal Processing in Medicine and Biology Symposium (SPMB), IEEE, XP032566939, DOI: 10.1109/SPMB.2013. 6736772 [retrieved on Feb. 10, 2014], Dec. 7, 2013, pp. 1-6.
(Continued)

*Primary Examiner* — Devin B Henson
(74) *Attorney, Agent, or Firm* — Greenblum & Bernstein, P.L.C.

(57) ABSTRACT

The present invention concerns the field of medical technology and relates to a device for the measurement, diagnosis, and/or therapy of the strength of the human finger, hand, arm, and/or shoulder, as can for example be used to measure bending strength. The object of the invention is to specify a device with which a multi-functional measurement, diagnosis, and/or therapy of the strength of the human
(Continued)

finger, hand, arm, and/or shoulder is possible on one device. The object is attained by a device composed at least of a base plate and force-measuring sensors, of which at least one sensor comprises a puller bolt passing therethrough and this force-measuring sensor is positioned in a stationary manner on one side of the base plate and is connected to an actuation part in a force-fit via the puller bolt, furthermore in the region of the base plate a guide for additional force-measuring sensors is present and movable auxiliary devices can also be present.

20 Claims, 4 Drawing Sheets

(51) Int. Cl.
*A63B 21/00* (2006.01)
*A63B 23/035* (2006.01)
*A63B 23/12* (2006.01)
*A63B 23/16* (2006.01)
*A63B 23/14* (2006.01)
*A61H 1/02* (2006.01)

(52) U.S. Cl.
CPC .......... *A61B 5/6825* (2013.01); *A61B 5/6826* (2013.01); *A61B 5/6835* (2013.01); *A61H 1/0274* (2013.01); *A63B 21/4035* (2015.10); *A63B 23/03508* (2013.01); *A61B 2562/0252* (2013.01); *A61B 2562/0261* (2013.01); *A63B 23/1245* (2013.01); *A63B 23/1281* (2013.01); *A63B 23/14* (2013.01); *A63B 23/16* (2013.01)

(58) Field of Classification Search
CPC .......... A61B 5/6835; A61B 2562/0252; A61B 2562/0261; A63B 21/4035; A63B 23/03508; A63B 23/1245; A63B 23/1281; A63B 23/14; A63B 23/16; A61H 1/0274; A61H 1/0277; A61H 1/0281; A61H 1/0285

See application file for complete search history.

(56) References Cited

U.S. PATENT DOCUMENTS

| | | | | |
|---|---|---|---|---|
| 6,948,502 | B2* | 9/2005 | Berger | ................ A61B 6/0421 128/845 |
| 6,951,529 | B1* | 10/2005 | Ware | ..................... A63B 21/06 482/45 |
| 8,082,786 | B1* | 12/2011 | Akins | .................... A61B 5/221 73/379.01 |
| 2012/0255355 | A1* | 10/2012 | Xu | ......................... A61B 5/225 73/379.02 |
| 2013/0060171 | A1* | 3/2013 | Fu | ............................ A61H 1/02 601/5 |

FOREIGN PATENT DOCUMENTS

| | | |
|---|---|---|
| EP | 0 495 461 | 7/1992 |
| WO | 2011/044 520 | 4/2011 |

OTHER PUBLICATIONS

L.C. Miller et al., "A Wrist and Finder Force Sensor Module for Use During Movements of the Upper Limb in Chronic Hemiparetic Stroke", IEEE Transactions on Biomedical Engineering, IEEE Service Center, Piscataway, NJ, USA, vol. 56, No. 9, XP011343045, ISSN: 0018-9294, DOI: 10.1109/TBME.2009.2026057, Sep. 1, 2009, pp. 2312-2317.
Int'l Search Report (form PCT/ISA/210) conducted in Int'l Appln. No. PCT/EP2017/061344 (dated Sep. 13, 2017) (w/ Translation).
German Office Action conducted in counterpart German Appl. No. DE 10 2016 208 443, dated Jan. 24, 2017 (w/ Machine Translation).
Int'l Prelim. Exam. Rpt. & Written Opinion (form PCT/IB/373; PCT/ISA/237) conducted in Int'l Appl. No. PCT/EP2017/061344 dated Nov. 20, 2018 (Translation).

* cited by examiner

# DEVICE FOR MEASUREMENT, DIAGNOSIS AND/OR THERAPY OF THE STRENGTH OF THE HUMAN FINGER, HAND, ARM AND/OR SHOULDER

CROSS-REFERENCE TO RELATED APPLICATIONS

The present application is a U.S. National Stage of International Patent Application No. PCT/EP2017/061344 filed May 11, 2017, and claims priority of German Patent Application No. 10 2016 208 443.7 filed May 17, 2016.

BACKGROUND OF THE INVENTION

1. Field of the Invention

The present invention concerns the field of medical technology, medical diagnosis, physical therapy, and medical rehabilitation, and relates to a device for the measurement, diagnosis, and/or therapy of the strength of the human finger, hand, arm, and/or shoulder, as can for example be used to measure the bending strength of the hand or arm, to identify problems with the bending of the hand or arm, and to remedy these problems.

2. Discussion of Background Information

A device with which the bending strength of the human hand or the index through little finger and the various bending angles can be measured is known from DD-PS 204 206. The measurement of this strength is achieved in that the grip parts can be freely chosen on lines positioned perpendicularly to one another and a grip part that is grasped by the index through little finger and can be vertically adjusted to the height of each finger is operatively engaged with a force-measuring sensor (transducer). The movable grip part is connected to a puller bolt which comprises on its opposite end a flange that, under the force of a compression spring, bears against the central region of the pressure load cell which surrounds the puller bolt coaxially without tilting. However, an error-free measurement of the bending strength of the thumb is not possible with this device.

Measurement of the bending strength of the thumb becomes possible with a device according to DE-PS 36 34 940, in which, with the use of the aforementioned design, the horizontal and vertical angle of the longitudinal axis of a hand grip and brace to the longitudinal axis of the puller bolt operatively engaged with the transducer and the inclination thereof relative to the horizontal plane in a second vertical plane located perpendicularly to the first vertical plane are freely adjustable by means of a swiveling stand and two hinges, and the longitudinal and transverse distance of the hand grip to the finger-pull grip connected to the puller bolt are freely adjustable with the aid of a longitudinal support and a transverse support.

Although the known devices enable exact measurements of the bending strength of the human hand or individual fingers, in each case precisely in the effective direction of the force in biomechanically identical conditions, for hands of a different size, and at different bending angles of the fingers on one and the same hand, said devices do not permit measurement of the stretching strength of the human hand or the individual fingers thereof, which stretching strength is important for the different fields of medicine.

From U.S. Pat. No. 3,680,386 A, a measurement device is known with which the magnitude of an impact force and also a pulling force for body parts can be measured.

According to EP 0 495 461 A1, a device is also known for measuring the strength of the human hand or the individual fingers thereof by means of a force-measuring sensor, in which device the force-measuring sensor comprises a puller bolt passing therethrough and is surrounded by a housing, wherein a reversing disk is provided which is braced against the housing when bending forces or pulling forces are applied with an actuation part and against the force-measuring sensor when stretching forces or compressive forces are applied with an actuation part.

Force-measuring sensors are force transducers with a measuring function. Force transducers are also referred to as force sensors, wherein the force that acts on a sensor is measured. Generally known force-measuring sensors are spring-bellows force transducers, piezo force transducers, force transducers with vibrating elements, force transducers with electromagnetic compensation, and resistive force transducers (German-language Wikipedia keyword "Kraftaufnehmer").

A disadvantage of the known technical solutions is that a multi-functional measurement, diagnosis, and/or therapy of the strength of the human finger, hand, arm, and/or shoulder is not possible on one device.

SUMMARY OF THE EMBODIMENTS

The object of the invention is the specification of a device for the measurement, diagnosis, and/or therapy of the strength of the human finger, hand, arm, and/or shoulder, with the aid of which device a multi-functional measurement, diagnosis, and/or therapy of the strength of the human finger, hand, arm, and/or shoulder is possible on one device.

The object is attained by the invention disclosed in the claims. Advantageous embodiments are the subject of the dependent claims, wherein the invention also includes combinations of the individual dependent claims within the meaning of an AND-operation, provided that they are not mutually exclusive.

The device according to the invention for the measurement, diagnosis, and/or therapy of the strength of the human finger, hand, arm, and/or shoulder is composed at least of a base plate and force-measuring sensors, of which at least one sensor comprises a puller bolt passing therethrough, and this force-measuring sensor is positioned in a stationary manner on one side of the base plate and this force-measuring sensor is connected to an actuation part in a force-fit via the puller bolt, furthermore a guide for additional force-measuring sensors is present on the side of the base plate opposite of the force-measuring sensor positioned in a stationary manner and at least partially in the region of the base plate sides adjoining said side, and furthermore also axially and/or radially movable auxiliary devices can be present at and/or on the base plate, which auxiliary devices can be used to position the fingers, hand, and/or arm and/or can serve as a brace.

Advantageously, the force-measuring sensors of the device according to the invention are spring-bellows force transducers, piezo force transducers, transducers with vibrating elements, force transducers with electromagnetic compensation, and/or strain-gauge force transducers.

Advantageously, a finger grip part, hand grip part, hand rest, thumb rest, and/or elbow tray is also present as an actuation part of the device according to the invention, wherein these actuation parts are shaped for the individual fingers for the right or left hand, arm, and/or shoulder.

More advantageously, device elements are present for the hand grip part, which elements achieve the stationary positioning of the fingers during the measurement and/or therapy.

Advantageously, releasable connecting elements, bolts, locking screws, and/or grip recesses are present as device elements.

The force-fitting connection between the puling bolt and actuation part is advantageously achieved via a quick-release fastener or locking screw.

Also, a rectangular plate made of wood and/or plastic and/or metal, with or without cushioning elements, is used as a base plate.

More advantageously, a base plate is present, the cross section of which is adapted or adaptable to the forearm shape and/or hand shape across the length of the base plate.

Furthermore, the guide is advantageously present on the side of the base plate opposite of the force-measuring sensor positioned in a stationary manner, in the form of a U-shaped metal rail at the edge of the base plate or in the form of a groove at the outer edge of the base plate. And also advantageously, the guide is used to receive a fastening device for one or more force-measuring sensors, wherein these sensors are arranged such that they can be displaced and fixed in place on or at the guide.

Advantageously, the axially movable auxiliary devices are present for the positioning and/or as a brace for measuring and/or training the fingers, hand, and/or arm.

Also advantageously, the radially movable auxiliary devices are present for the positioning and/or as a brace for measuring and/or training the fingers, hand, arm, and/or shoulder.

Likewise advantageously, a hand rest, a thumb rest, and/or an elbow tray are present as auxiliary devices, wherein these auxiliary devices are shaped for the right or left hand, right or left thumb, and/or right or left elbow.

Advantageously, immobilizing elements for the fingers, hand, arm, and/or elbow are present as auxiliary devices.

As auxiliary devices, a holding device fixed in place in the region of the stationary force-measuring sensor is also advantageously positioned for an additional force-measuring sensor, wherein this holding device positions an additional force-measuring sensor to the right and/or left of the base plate in the region of the thumb and/or the hand, and is designed to absorb the force of the thumb strength and/or torsional strength of the hand and/or forearm.

With the device according to the invention, the bending, pulling, stretching, torsional, and/or compressive strength of the human finger, hand, arm, and/or shoulder are advantageously measurable and/or trainable.

The use according to the invention of a device for the measurement, diagnosis, and/or therapy of the strength of the human finger, hand, arm, and/or shoulder is for measuring and/or training the bending, pulling, stretching, torsional, and/or compressive strength of the human finger, hand, arm, and/or shoulder.

Advantageously, the device according to the invention is used in order to measure, give therapy to, and/or train the strength of the muscles of the finger, hand, arm, and/or shoulder. More advantageously, the device according to the invention is used to measure, give therapy to, and/or train the strength of the biceps, triceps, and/or deltoid muscle.

With the present invention, it is for the first time possible to specify a device with which the measurement, diagnosis, and/or therapy of the strength of the human finger, hand, arm, and/or shoulder is possible on one device.

Based on the device known per se for measuring the strength of the human hand or the individual fingers thereof according to EP 0 495 461 A1, the device has been enhanced according to the invention to the effect that it can be implemented not only for the measurement, but also for the diagnosis and/or therapy of the strength, and that with the device the measurement, diagnosis, and/or therapy of the strength of the arm and/or the shoulder can be also be achieved.

The device known per se is composed of a force-measuring sensor which comprises a puller bolt that passes therethrough and is surrounded by a housing, wherein an actuation part for the application of bending forces or pulling forces is connected in a force-fit to the puller bolt, wherein a hand rest is provided as a brace for the application of bending forces and pulling forces, wherein an actuation part for the application of stretching forces or compressive forces is connected in a force-fit to a reversing disk, wherein an elbow brace is provided for the application of stretching forces or compressive forces, wherein the reversing disk is braced against the housing when bending forces or pulling forces are applied, wherein the puller bolt is displaceable relative to the reversing disk and the force-measuring sensor in an axial direction, and wherein the reversing disk is braced against the force-measuring sensor when stretching forces or compressive forces are applied, wherein the reversing disk and the force-measuring sensor are displaceable relative to the puller bolt and housing.

Based on this, with the device according to the invention the strength of the entire arm, including the shoulder, can on the one hand now be measured in various radial or axial directions, both on the right and also on the left arm, and problems can on the other hand be diagnosed and therapy then also given for said problems.

The strength values to be obtained can, in combination with anthropometric measured values, render it possible to make statements about a person's physical development. These statements can be used as a normative basis for evaluating the fitness and medical condition of those people who suffer from diseases that impair the functioning of the shoulder joint.

The increase in shoulder strength is the source of the additional improvements to the fitness of the shoulder. Focused training results in an increase in the strength of the shoulder muscles. The strengthened muscles can then relieve stress on the joint socket and joint capsule. In this manner, subsequent symptoms of wear and tear are reduced and potential causes or foci of inflammation are eliminated. This in turn promotes movement and enables a continually improving training effort. Strength continues to increase, and the mobility of the shoulder and the entire arm and the hand gradually improves. Successful training is thus caused by the increase in strength. The result of this is the recovered quality of life that is the consequence of the improved range of use of the arm.

With the solution according to the invention, both pulling strength and also compressive strength and thus the bending as well as the stretching, torsional, and compressive strength of the human hand or individual fingers, of the arm, or of the shoulder can be measured, diagnosed and given therapy accurately and with comparatively little effort, and can thus be trained. The use of the device is thereby not solely limited to medical tasks. The device can also be used in other technical systems where forces must be measured in opposing directions.

With the device according to the invention, it is particularly advantageous that the device can be adapted with little effort to the anatomy of the individual human body, and that the various stated measurement, diagnostic, and therapeutic options can be implemented.

In order for it to be possible to perform a most accurate possible measurement, the force-measuring sensors are designed as sensors with the smallest possible contact surfaces, and frictionally induced measurement inaccuracies are minimized by the sensors' positioning on the device according to the invention.

The device according to the invention is thereby composed at least of a base plate, which is advantageously rectangularly shaped and made of wood and/or plastic and/or metal, with or without cushioning for the parts of the human arm and/or hand resting thereupon. This base plate can also, in cross section, be adapted to the forearm shape and/or hand shape of the human body across the length of the base plate, or can be adaptable to the respective specific forearm and/or hand shape of the patient.

Auxiliary devices can also be attached on or at the base plate. Such as, for example, a hand rest, a thumb rest, and/or an elbow tray, wherein these auxiliary devices can be shaped for the right or left hand, right or left thumb, and/or right or left elbow. These auxiliary devices serve as immobilizing elements for the fingers, hand, arm, and/or elbow and/or as braces.

These auxiliary devices usable according to the invention can be anatomically shaped elements that are used for positioning and/or immobilization or serve as a brace during measurement, diagnosis, and/or therapy.

The attachment of the auxiliary devices thereby takes place by means of releasable connections, bolts, fixing screws, or a quick-release fastener.

The force-measuring sensors of the device according to the invention can be spring-bellows force transducers, piezo force transducers, transducers with vibrating elements, force transducers with electromagnetic compensation, and/or strain-gauge force transducers.

The device according to the invention furthermore comprises at least one force-measuring sensor that is positioned in a stationary manner on one side of the base plate and a puller bolt that passes therethrough, which puller bolt is in turn connected in a force-fit to an actuation part.

A finger grip part, hand grip part, hand rest, thumb rest, and/or elbow tray can be present as an actuation part, wherein the shape of the actuation parts can be anatomically adapted to the human body, for example, for the individual fingers for the right or left hand, the arm, and/or the shoulder. The actuation part can thereby be a finger grip part, hand grip part, hand rest, thumb rest, and/or an elbow tray.

The attachment of the actuation part can thereby also take place by means of releasable connections, bolts, fixing screws, or a quick-release fastener.

The actuation part can advantageously be combined with a finger grip part and used with a hand rest as an auxiliary device. The hand rest is used so that the force only comes from the finger, and so that other forces from the hand, arm, or entire human body are not measured. Likewise, a hand rest can be used in combination with an elbow tray as an auxiliary device, in order to hold the forearm in position for measuring the shoulder strength.

If the strength of the hand is being measured, diagnosed, and/or given therapy, a hand grip is advantageously used which positions the fingers of the hand in a stationary manner so that the fingers cannot slide together and press on one another during the measurement, diagnosis, and/or therapy.

To enable this stationary positioning of the fingers on the hand grip, releasable connecting elements, bolts, locking screws, and/or grip recesses can be present, and/or the hand grip can comprise an arch that resembles the hand shape with bent fingers, and/or the hand grip can be adjustable to the width of all of the fingers in a stationary manner from both sides of the fingers (on the side of the index finger and of the little finger) with limiting devices.

With the device according to the invention, it is also possible to measure the strength of the thumb. Likewise, the hand grip can advantageously also be obliquely fixed in place, so that a measurement, diagnosis, and/or therapy can also be performed for people whose thumb and/or hand and/or arm motion is limited.

Furthermore, the base plate comprises a guide for at least one additional force-measuring sensor, in order to allow the multi-functional measurement, diagnosis, and/or therapy of the different strengths to be performed on the fingers, hand, arm, or shoulder.

The guide is thereby present on the side of the base plate opposite of the force-measuring sensor positioned in a stationary manner and at least partially in the region of the base plate sides adjoining said side.

The guide can thereby be implemented by a U-shaped metal rail or groove, in each case at the outer edge of the base plate. This guide receives a fastening device for at least one additional force-measuring sensor, wherein according to the invention, this force-measuring sensor can be displaced and fixed in place on or at the base plate. In this manner, the force-measuring sensor is guided on and/or at the base plate and is thus displaceable and fixable in multiple positions along the U-shaped metal rail or groove in order to allow the various strengths to be measured on the fingers, hand, arm, or shoulder.

In this way, the force-measuring sensor can be guided around the forearm. More precisely, this means that neither does the device need to be rotated, nor does the patient need to change the sitting position for measurements of all shoulder strengths on an arm. To avoid the problem of force dissipation during anteversion strength measurement, the previously used knob can be replaced by an ergonomically optimal wooden grip that can be placed on a mount so that the direct, straight-line transmission of force into the force-measuring sensor can take place. The new wooden grip is available in different sizes, so that the use of wooden grips of varying size for differently sized hands is possible. More accurate measured values can thus be obtained, since virtually the entire force can now be transferred to the force-measuring sensor in an undivided manner. The second force-measuring sensor is used for the measurement of retroversion and abduction strength. In this case, the torque on the upper arm starting in the forearm is eliminated in the abduction measurement, since the force-measurement sensor is positioned precisely at the desired measurement point of the upper arm, the lateral epicondyle. For retroversion, instead of the previous semicircular, concave wooden elbow tray, a molded wooden tray ergonomically adapted to the distal end of the upper arm is used as an auxiliary device that enables a transmission of force in the region of the epicondyles (lateral epicondyle and medial epicondyle). With the device according to the invention, a pinpoint, direct transmission of force into the two force-measuring sensors is achieved.

A standardized transmission of force for different arm dimensions is, on the one hand, enabled in that the position of the displaceable force-measurement sensor can be adjusted once in a vertical direction and twice in a horizontal direction. On the other hand, a further ergonomic adaptation occurs in that force-measurement sensing elements that are significantly better adapted to the arm shape than before can be used in various arm sizes for measuring the strength during abduction and retroversion. Additionally, different grip sizes for various hand sizes are available for measuring the strength during anteversion.

To standardize the measurement, biomechanically identical measuring conditions for arms of varying length must be created, in that the transmission of force to the measurement system takes place at the same anatomical point, in contrast to the previous approach. The lateral epicondyle was selected as an anatomical reference point for the transmission of force for measuring the arm strength during abduction. To measure the arm strength during retroversion, the outer line on the upper arm from the lateral epicondyle to the medial epicondyle is the anatomic reference line for the transmission of force.

The positioning of the movable force-measuring sensor is composed of the U-shaped guide with a slide that can be moved horizontally in an infinitely variable manner. The vertical adjustability can be achieved in that the slide is composed of two metal bars connected to one another at a right angle and the force-measuring sensor is movably connected to the vertical leg of the slide. The support can be fixed to the U-shaped guide with the aid of a bolt in order to allow the support to be guided and fixed in place in an infinitely variable manner around the arm resting in position. The movable force-measuring sensor can, in every freely selectable position, be securely screwed down on both sides and at the end of the base plate behind the elbow. In this manner, the force-measuring sensor can be adjusted twice in a horizontal direction and once in a vertical direction.

An additional movable force-measuring sensor can be positioned on a holding device fixed in place in the region of the stationary force-measuring sensor, wherein the holding device can be designed in a double-angle shape and can be attached such that it can be pivoted from the left side to the right side of the base plate. With this holding device, the additional movable force-measuring sensor can achieve the measurement, diagnosis, and/or therapy of the thumb strength of the right or left hand. Likewise, the measurement, diagnosis, and/or therapy of the torsional strength of the hand and/or the forearm is possible with the aid of a grip used as an additional auxiliary device, which grip positions the hand and/or the forearm at different angles and exerts forces on the force-measuring sensor.

The device according to the invention for the measurement, diagnosis, and/or therapy of the strength of the human finger, hand, arm, and/or shoulder is used for measuring and/or training the bending, pulling, stretching, torsional, and/or compressive strength of the human finger, hand, arm, and/or shoulder.

The use of the device on a patient thereby advantageously takes place in two major phases. Each is characterized by a multiple alternation between an exertion of strength and a rest, wherein the rests in the second major phase are significantly shorter than in the first. As the increase in strength progresses, the rests are shortened over the further course of treatment. Before the start of the entire training or exercise treatment, the starting level of the hand closing strength on the left and right side is documented, in order to record the initial state of strength performance. If only one hand is crippled, the performance of the healthy hand can serve as the target for the ailing hand. Here, it must be kept in mind whether the patient is left- or right-handed. The primary hand must have a roughly five- to ten-percent greater hand closing strength than the secondary hand. This must be taken into account when setting the training goal. Depending on the strength deficit, all individual fingers or only some fingers are treated, in each case on the middle and distal phalanx. However, the hand closing strength of the middle phalanges is nearly always, and often also of the distal phalanges, trained in combination with the focus on individual fingers. It should be noted that the treatment is specifically adapted to each patient in accordance with the injury pattern. Training usually takes place twice a week, each for a total time of 45 to 60 minutes with an exercise or training of five to six individual functions. The training intensity is always adapted to the patient's performance level. In order to ensure optimal strength development, the device is fixed in place on the table using screw clamps. The patient sits parallel to the device in an upright bodily posture, on a non-rolling and height adjustable chair. This chair is preferably adjusted such that the patient has his/her arm laying virtually in the neutral zero position in the forearm tray and can clasp the grip parts.

Advantageously, the strength of the finger, hand, arm, and/or shoulder muscles is measured, given therapy, and/or trained, wherein advantageously the measurement, therapy, and/or training of the strength of the biceps, triceps, and/or deltoid muscle occurs.

The device with the actuation parts according to the invention enables an accurate measurement of the strength in the individual fingers, hand, arm, and/or shoulder, in particular through the use of the enhanced device components and auxiliary devices.

With regard to the measurement of the strength in the shoulder joint, an accurate measurement of the strength is now possible on the arm in the three directions of movement anteversion, retroversion, and abduction with the device according to the invention.

With the device according to the invention, the strength and flexibility of the individual fingers, hand, arm, and/or shoulder can be given therapy.

BRIEF DESCRIPTION OF THE DRAWINGS

The device according to the invention is explained in greater detail below with the aid of multiple exemplary embodiments.

In this Matter

DETAILED DESCRIPTION OF THE EMBODIMENTS

Example 1

Figure 1:
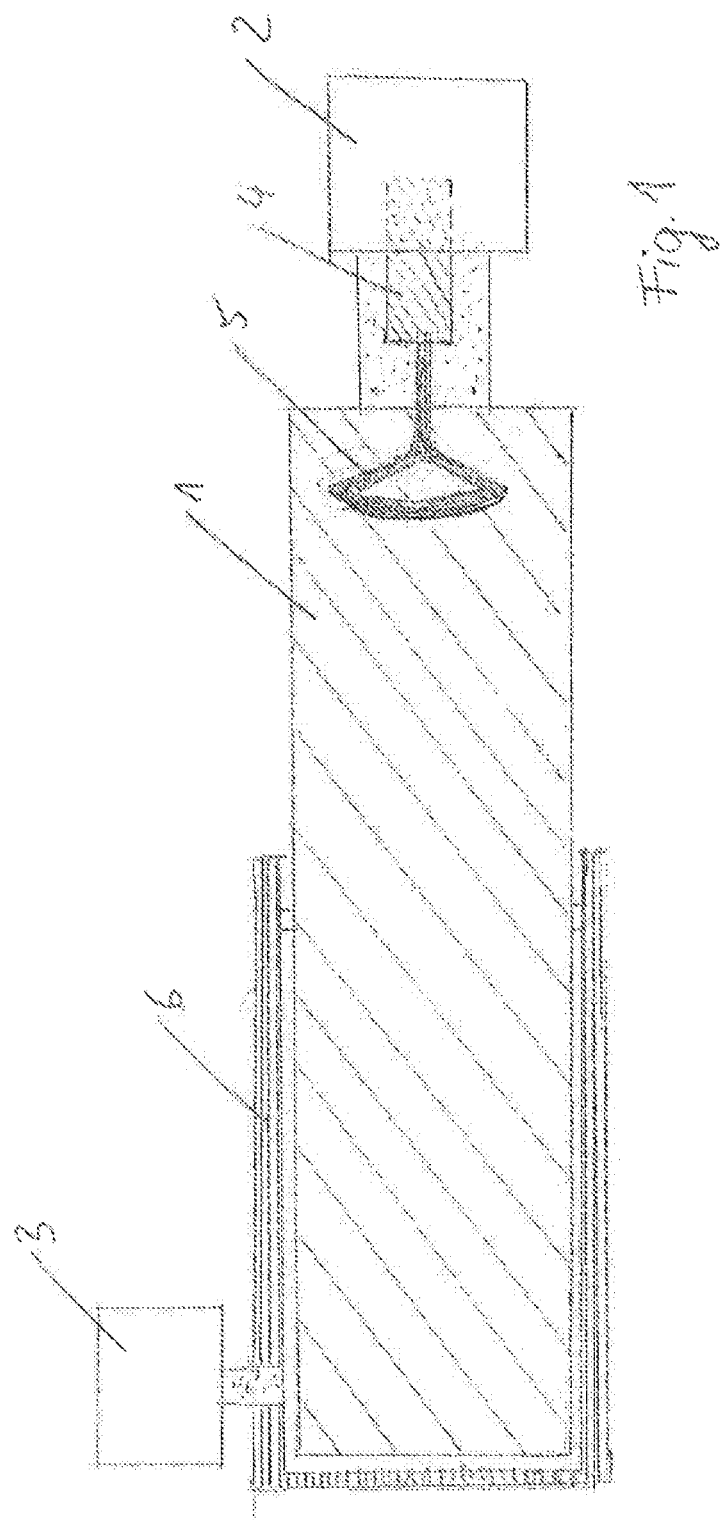
FIG. 1 shows a schematic overall view of the device according to the invention, with a hand grip part as an actuation part.

The device according to FIG. 1 comprises a rectangular base plate 1 of wood with the dimensions W×L×H=60×20×3 cm, wherein two force-measuring sensors 2 and 3 are arranged on the base plate 1. One force-measuring sensor 2 is positioned in a stationary manner on the one short side of the rectangular base plate 1 via a metallic connection and comprises a puller bolt 4 passing through the sensor. The other force-measuring sensor 3 is arranged by means of a metallic connection on the U-shaped guide 6 such that the sensor is displaceable in both an axial and also in a radial direction with respect to the base plate. The U-shaped guide 6 is made of metal, and is guided 30 cm along each of the longitudinal sides of the rectangular base plate 1 and attached to the base plate 1.

The puller bolt 4 passing through the stationary force-measuring sensor 2 is connected in a force-fit to an actuation part 5 in the form of a hand grip 20.

On the base plate 1, a forearm cushion is attached as an auxiliary device, on which cushion the forearm is positioned, wherein the cushion also serves as a stationary form of immobilization of the forearm. Additionally, as an auxiliary device an immobilizing device composed of adjustable rods and screws is attached to the base plate 1 at the height of the wrist, which immobilizing device immobilizes the forearm as much as possible during the measurement/diagnosis/therapy, so that the force can be measured along the axis of the forearm when the hand exerts its strength on the hand grip 20.

A finger grip part can be arranged in place of the hand grip part. In this case, a hand rest, for example, a bolt, is advantageously present in order to perform the measurement, diagnosis, and/or therapy for the finger and minimize forces coming from the hand, arm, or entire human body.

Advantageously, a finger grip part 21, hand grip part 22, hand rest 23, thumb rest 24, and/or elbow tray 25 is also present as an actuation part 5 of the device according to the invention, wherein these actuation parts 5 can be anatomically adapted to the human body, for example, for the individual fingers for the right or left hand, the arm, and/or the shoulder. More advantageously, device elements are present for the hand grip part 22, which elements achieve the stationary positioning of the fingers during the measurement and/or therapy, see, e.g., FIG. 2.

Advantageously, releasable connecting elements 30, bolts 31, locking screws 32, and/or grip recesses 33 are present as device elements.

The force-fitting connection 35 between the pulling bolt 4 and actuation part 5 is advantageously achieved via a quick-release fastener 36 or locking screw 37.

Also, a rectangular plate made of wood and/or plastic and/or metal, with or without cushioning elements, is used as base plate 1.

More advantageously, via anatomically shaped elements 43, base plate 1 can be adapted or adaptable to the forearm shape and/or hand shape across the length of the base plate.

Advantageously, the axially movable auxiliary devices are present for the positioning and/or as a brace for measuring and/or training the fingers, hand, and/or arm.

Also advantageously, the radially movable auxiliary devices are present for the positioning and/or as a brace for measuring and/or training the fingers, hand, arm, and/or shoulder.

Auxiliary devices 10 can also be attached on or at base plate 1. Such as, for example, a hand rest 40, a thumb rest 41, and/or an elbow tray 42, wherein these auxiliary devices can be shaped for the right or left hand, right or left thumb, and/or right or left elbow. These auxiliary devices 10 serve as immobilizing elements for the fingers, hand, arm, and/or elbow and/or as braces.

These auxiliary devices usable according to the invention can be anatomically shaped elements 43 that are used for positioning and/or immobilization or serve as a brace during measurement, diagnosis, and/or therapy.

The attachment of the auxiliary devices thereby takes place by releasable connections, bolts, fixing screws, or a quick-release fastener.

Figure 2:
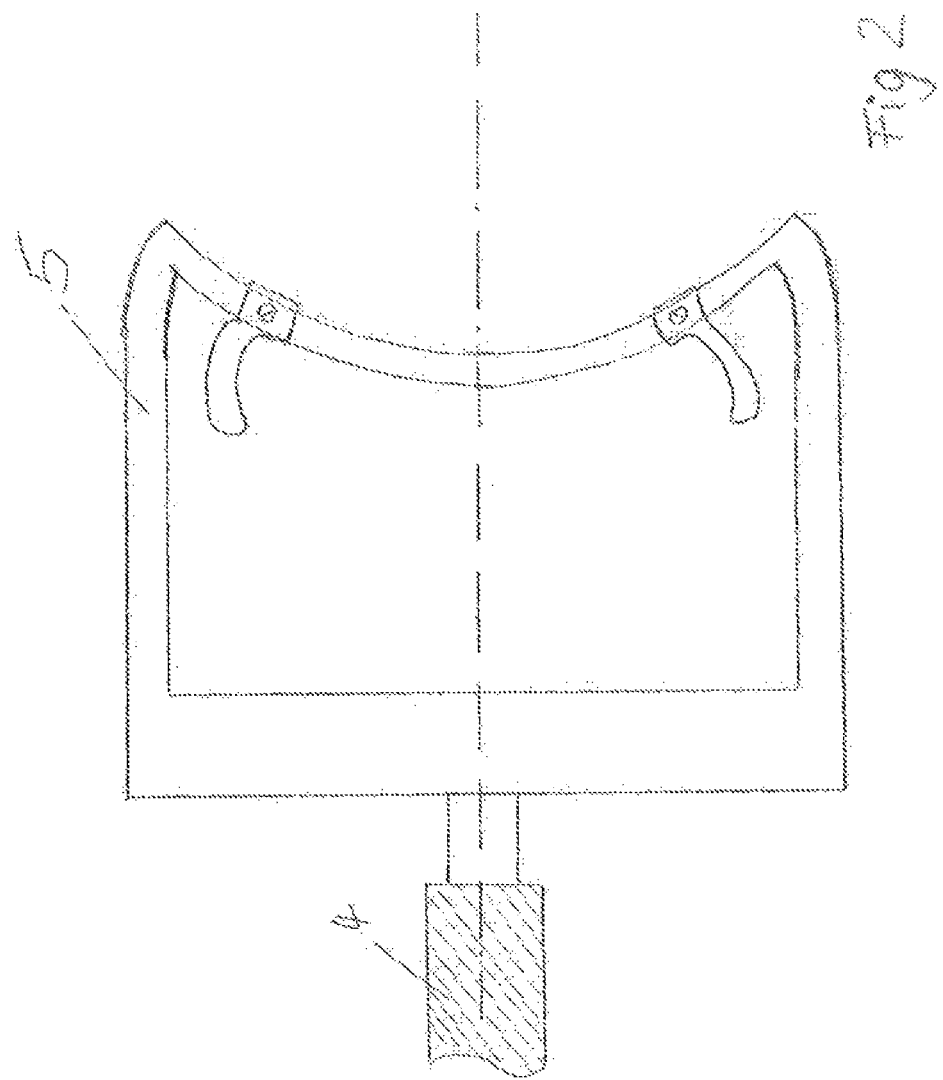
FIG. 2 shows a schematic detailed view of the advantageous hand grip part as an actuation part.

If the strength of the hand is being measured, diagnosed, and/or given therapy, a hand grip is advantageously used which positions the fingers of the hand in a stationary manner so that the fingers cannot slide together and press on one another during the measurement, diagnosis, and/or therapy. To enable this stationary positioning of the fingers on the hand grip, releasable connecting elements, bolts, locking screws, and/or grip recesses can be present, and/or the hand grip can comprise an arch that resembles the hand shape with bent fingers, as shown in FIG. 2 and/or the hand grip can be adjustable to the width of all of the fingers in a stationary manner from both sides of the fingers (on the side of the index finger and of the little finger) with limiting devices, as also shown in FIG. 2.

Example 2

On the base plate 1 according to example 1, an elbow tray displaceable in an axial direction on the base plate 1 is additionally attached as an auxiliary device on the side opposite of the stationary force-measuring sensor 2, which tray serves as a form of immobilization of the elbow and as a brace.

After the positioning of the forearm on the base plate 1 and immobilization of the wrist and elbow, the measurement of the abduction of the shoulder is performed by measuring the force laterally on the elbow with the force-measuring sensor 3 positioned on the guide 6, wherein the force-measuring sensor 3 was moved to the position of the elbow beforehand. A forearm cushion and hand rest, by means of which the immobilization of the wrist takes place, are located on the base plate 1. The forearm is positioned on forearm rest and the hand grasps the hand rest, the force-measuring sensor then measures the strength of the shoulder when a force is exerted by the elbow on the force-measuring sensor.

Figure 3:
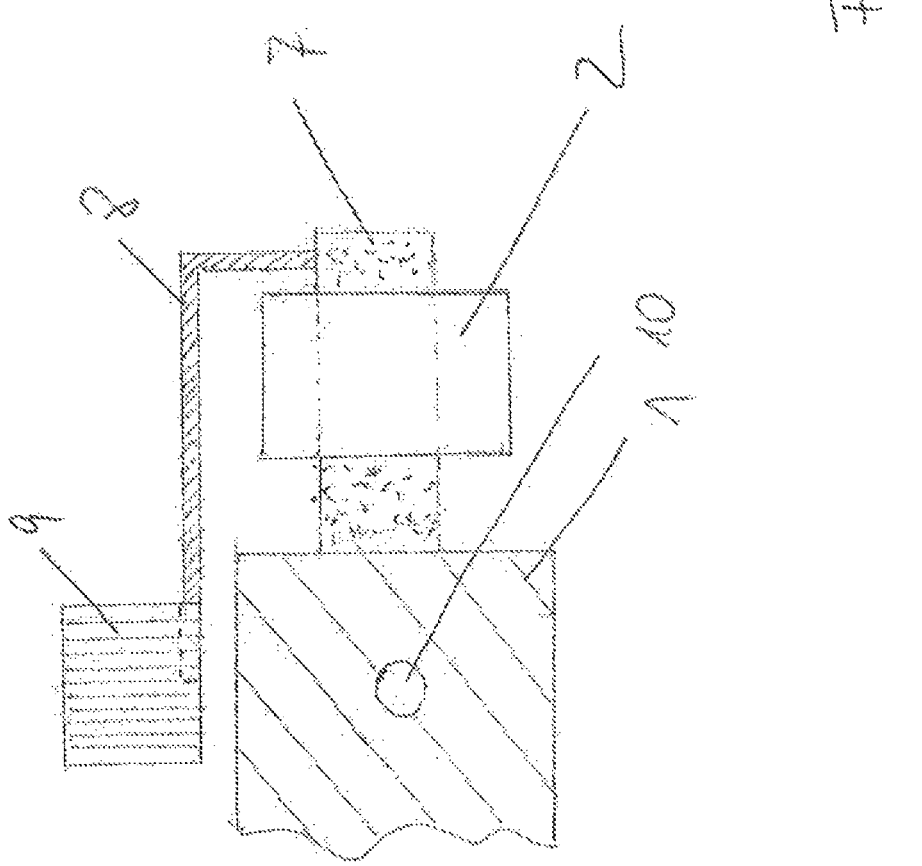
FIG. 3 shows a schematic detailed view of the advantageous arrangement with an additional force-measuring sensor for the measurement diagnosis, and/or therapy of the thumb strength of the right or left hand and/or the torsional strength of the hand and/or forearm with the aid of a grip used as an additional auxiliary device.
Figure 4:
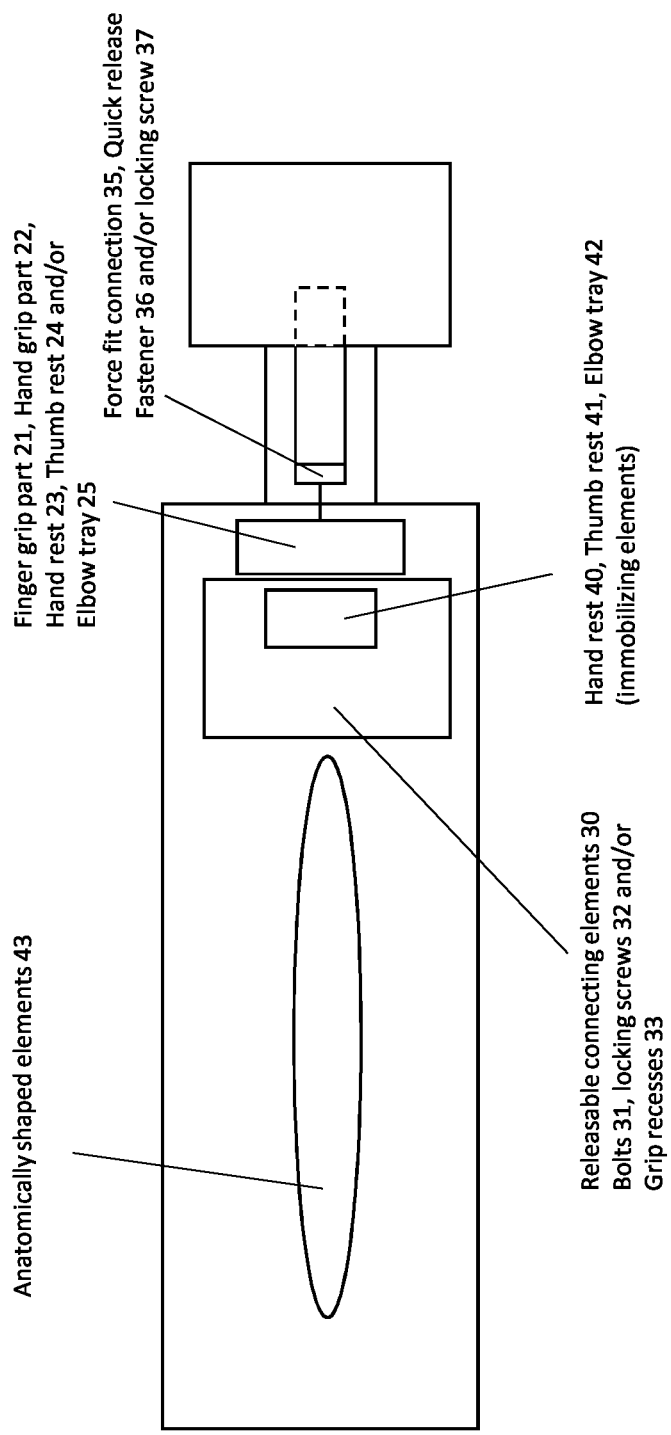
FIG. 4 shows a schematic view of alternative embodiments of the actuation parts and auxiliary parts according to embodiments.

Moreover, as shown in FIG. 3, an additional movable force-measuring sensor can be positioned on a holding device fixed in place in the region of the stationary force-measuring sensor, wherein the holding device can be designed in a double-angle shape and can be attached such that it can be pivoted from the left side to the right side of the base plate. With this holding device, the additional movable force-measuring sensor can achieve the measurement, diagnosis, and/or therapy of the thumb strength of the right or left hand. Likewise, the measurement, diagnosis, and/or therapy of the torsional strength of the hand and/or the forearm is possible with the aid of a grip used as an additional auxiliary device, which grip positions the hand and/or the forearm at different angles and exerts forces on the force-measuring sensor.

LIST OF REFERENCE NUMERALS

1 Base plate
2 Force-measuring sensor
3 Force-measuring sensor
4 Puller bolt
5 Actuation part
6 Guide 7 Support
8 Holding device
9 Movable force-measuring sensor
10 Grab handle as an auxiliary device
21 Finger grip part
22 Hand grip part,
23 Hand rest
24 Thumb rest
25 Elbow tray
30 Releasable connecting elements
31 Bolts
32 Locking screws
33 Grip recesses
35 Force fit connection
36 Quick release Fastener
37 Locking screw
40 Hand rest
41 Thumb rest
42 Elbow tray
43 Anatomically shaped elements

The invention claimed is:

1. A device for measurement, diagnosis, and therapy of strength of at least one human finger, a hand, an arm, or a shoulder, comprising:
  a base plate having a first longitudinal end and a second longitudinal end opposite the first longitudinal end, and a first lateral side and a second lateral side arranged opposite each other and adjoining the first longitudinal end;
  force-measuring sensors, wherein at least one of the force-measuring sensors is a stationarily positioned force-measuring sensor on the first longitudinal end of the base plate that comprises a puller bolt passing through the stationarily positioned force-measuring sensor;
  an actuation part connected to the at least one force-measuring sensor in a force-fit via the puller bolt;
  a guide for additional force-measuring sensors has three sides, such that the guide is positioned on the second longitudinal end of the base plate and at least partially in a region of the first and second sides of the base plate; and
  at least one of axially or radially movable auxiliary devices arranged at and/or on the base plate to position the at least one finger, hand, or arm or to serve as a brace,
  wherein the measurement and diagnosis of the strength of the at least one of a human finger, a hand, an arm, or a shoulder is performable on the device,
  wherein the three sides of the guide are configured to receive fastening devices for the additional force-measuring sensors so that the additional force-measuring sensors are displaceably fixable in place along the guide.

2. The device according to claim 1, wherein the force-measuring sensors are at least one of spring-bellows force transducers, piezo force transducers, transducers with vibrating elements, force transducers with electromagnetic compensation, or strain-gauge force transducers.

3. The device according to claim 1, wherein the actuation part comprises at least one of a finger grip part, hand grip part, hand rest, thumb rest, or elbow tray, which are shaped for at least one of individual fingers for the right or left hand, the arm, or the shoulder.

4. The device according to claim 3, wherein, when the actuation part comprises the hand grip part, stationary positioning of the fingers during the measurement and therapy is achieved.

5. The device according to claim 4, wherein the stationary positioning of the fingers is achieved via at least one of releasable connecting elements, bolts, locking screws, or grip recesses.

6. The device according to claim 1, wherein the force-fitting connection between the puller bolt and the actuation part comprises one of a quick-release fastener or locking screw.

7. The device according to claim 1, wherein the base plate comprises a rectangular plate made of at least one of wood, plastic or metal, with or without cushioning elements.

8. The device according to claim 1, wherein a cross section of the base plate is adapted or adaptable to a shape of a forearm and a shape of the hand across a length of the base plate.

9. The device according to claim 1, wherein the guide comprises one of a U-shaped metal rail at an edge of the base plate or a groove at an outer edge of the base plate.

10. The device according to claim 1, wherein, the device is further for training at least one human finger, a hand, an arm, or a shoulder, and
  wherein, for the measuring and the training, the at least one of the axially or radially movable auxiliary devices comprise axially movable auxiliary devices at least one of for positioning or bracing the at least one finger, the hand, the arm or the shoulder.

11. The device according to claim 1, wherein, the device is further for training at least one human finger, a hand, an arm, or a shoulder, and
  wherein, for the measuring and the training, the at least one of the axially or radially movable auxiliary devices comprise radially movable auxiliary devices at least one of for positioning or bracing the at least one finger, the hand, the arm or the shoulder.

12. The device according to claim 1, wherein the at least one of the axially or radially movable auxiliary devices comprise at least one of a hand rest, a thumb rest, or an elbow tray,
  wherein the at least one of the axially or radially movable auxiliary devices are shaped for the right or left hand, right or left thumb, and/or right or left elbow.

13. The device according to claim 1, wherein the at least one of the axially or radially movable auxiliary devices comprise immobilizing elements for at least one of the fingers, hand, arm, or elbow.

14. The device according to claim 1, further comprising a holding device fixed in place in a region of the stationary force-measuring sensor for one of the additional force-measuring sensor, wherein the holding device positions the one additional force-measuring sensor to at least one of the right or left of the base plate in a region of at least one of the thumb or the hand, and is designed to absorb a force of at least one of thumb strength or torsional strength of the hand and/or forearm.

15. The device according to claim 1, wherein a bending, pulling, stretching, torsional, or compressive strength of the at least one human finger, the hand, the arm, or the shoulder is measurable and trainable.

16. The device according to claim 1, wherein therapy of the strength of the at least one human finger, hand, arm, or shoulder is performable on the device.

17. A method using the device for the measurement, diagnosis, and therapy of the strength of the at least one human finger, the hand, the arm, or the shoulder according to claim 1, the method comprising:

measuring at least one of bending, pulling, stretching, torsional, or compressive strength of the at least one human finger, the hand, the arm, or the shoulder on the device; and training the at least one of the bending, pulling, stretching, torsional or compressive strength measured of the at least one human finger, the hand, the arm, or the shoulder on the device.

18. The method according to claim 17, further comprising measuring the strength of muscles of the at least one finger, the hand, the arm, or the shoulder on the device; and training of the strength measured muscles of the at least one finger, the hand, the arm, or the shoulder on the device.

19. The method according to claim 18, further comprising measuring the strength of the at least one of a biceps, triceps, and deltoid muscle on the device; and training the at least one of the strength measured biceps, triceps or deltoid on the device.

20. The method according to claim 17, wherein therapy of the strength of the at least one human finger, hand, arm, or shoulder is performable on the device.

\* \* \* \* \*